(12) United States Patent
Iyengar et al.

(10) Patent No.: US 7,640,847 B2
(45) Date of Patent: Jan. 5, 2010

(54) METHOD AND DEVICE FOR MEASURING THE TEXTURE OF COOKED GRAINS

(75) Inventors: Narashima Hampapura Venkatarama Iyengar, Mysore (IN); Sashikala Vadakkoot Balakrishnan, Mysore (IN); Vishwas Manoharrao Pratape, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 377 days.

(21) Appl. No.: 10/582,691

(22) PCT Filed: Jan. 31, 2003

(86) PCT No.: PCT/IN03/00443

§ 371 (c)(1),
(2), (4) Date: Mar. 7, 2007

(87) PCT Pub. No.: WO2005/064310

PCT Pub. Date: Jul. 14, 2005

(65) Prior Publication Data

US 2007/0259078 A1    Nov. 8, 2007

(51) Int. Cl.
*A23L 1/00*    (2006.01)
(52) U.S. Cl. .............. 99/335; 99/349; 99/485; 99/487
(58) Field of Classification Search ........... 99/485–493, 99/600–623, 342, 519–525, 326–335, 349; 241/9, 101.2, 222; 73/7, 78, 81, 592, 573, 73/37.5; 426/231–233
See application file for complete search history.

(56) References Cited

U.S. PATENT DOCUMENTS 4,703,647 A    11/1987    Behnke et al.
4,703,677 A *  11/1987    Rossini ................. 81/471

(Continued)

FOREIGN PATENT DOCUMENTS

FR    2 376 409 A    7/1978

(Continued)

*Primary Examiner*—Timothy F. Simone
(74) *Attorney, Agent, or Firm*—Ladas and Parry LLP

(57) ABSTRACT

A method and device for assessing end point of cooking of dhal and rice with good reproducibility are disclosed. Pulses are generally consumed as dhals after cooking to soft texture. Measurement of end point of cooking of dhals, rice etc is very subjective and current methods are not very satisfactory. An innovative device and an objective method for carrying out the same were developed. This works on the principle of determining the "spread area" during progressive cooking for dhals as well as rice, and reading the cooking time form a graph plotted. The device developed for the purpose can be used to exert the desired force for pressing the cooked grain and the area to which the grain spreads is determined by counting the number of squares from an appropriate graph sheet as "spread area" is plotted against the period of cooking a progressive increase was observed. The time at which, there was a sudden increase in the spread area or when a change in the slope of the curve (sudden deflection/steadiness) occurred was considered as cooking time of the sample (dhal/rice) being cooked. The method now reported corroborated well with the standard instrumental methods. This invention provides an objective and reliable method for assessing end point of cooking of dhal and rice with good reproducibility.

11 Claims, 2 Drawing Sheets

U.S. PATENT DOCUMENTS

| | | | | |
|---|---|---|---|---|
| 5,005,774 A | * | 4/1991 | Martin et al. | 241/101.2 |
| 5,285,681 A | * | 2/1994 | Binder et al. | 73/78 |
| 6,173,601 B1 | * | 1/2001 | Beekman et al. | 73/7 |
| 6,457,345 B1 | * | 10/2002 | Gebert et al. | 73/7 |

FOREIGN PATENT DOCUMENTS

| | | |
|---|---|---|
| JP | 57 147033 | 9/1982 |

\* cited by examiner

METHOD AND DEVICE FOR MEASURING THE TEXTURE OF COOKED GRAINS

FIELD OF THE INVENTION

The present invention relates to a method and device for measuring the texture of cooked grains. In particular, the present invention relates to a device for measuring the texture of cooked dhals (dehusked split pulse).

The invention is based on applying a pre-determined load to the grains and measuring the area to which the cooked grain spreads and computing the same as Spread Area. Pulses, especially red gram (tur), Bengal gram (channa), green gram (mung) and black gram (urad), are largely consumed in the form of 'dhal' (dehusked split pulse) after cooking to a soft texture.

BACKGROUND OF THE INVENTION

A large variability in the cooking quality of pulses or dhals has been observed among different pulses and even among different varieties of the same pulse. It has always been a difficult task to precisely assess the cooking quality of dhals. Current methods are very subjective. Generally, cooking quality of dhals is a function of cooking time i.e., time of boiling the dhal in excess water until it attains desired soft texture and is ready for consumption. Cooking quality has been shown as a function of water uptake, increase in volume after cooking, dispersibility of solids into water and textural softening during cooking and some of these could be used as indices of cooking. Textural softening and end point of cooking is judged by pressing the cooked dhal between two glass slides and taken as time at which 'there are no hard-centres'. Obviously this is quite subjective and varies from analyst to analyst and also cannot be easily quantified. Similarly the end point of cooking of rice is normally judged by pressing the cooked rice between two glass slides and the time at which there is disappearance of white core is taken as its cooking time. However, these are quite subjective and do not provide a quantitative method for direct measurement of texture of cooked grains (dhals/rice). Literature available for this and their limitations are reviewed here.

Reference may be made to the publication by Subba Rao et al (1964) who studied the effect of cooking conditions and chemicals on the cooking quality of several dhals. They have described a method for evaluating the cooking quality in terms of cooking time. A suggestion was also made that quantity of solids dispersed during cooking could be used as a measure of cookability of pulses when cooked as dhals. They showed that different dhals dispersed to different extents during cooking and hence could be used as a method for comparing the cookability of different dhals. However, this does not provide a method for measuring the cooked grain texture.

Narasimha and Desikachar (1978) made a study on the cooking quality of dhals from sixteen varieties of tur pulse (*Cajanus cajan*) in comparison with that of dhals from green gram and horse gram and showed that percent dispersed solids (% DS) during cooking correlated well with cooking time of the dhals. It was suggested that this could be used as an objective measure of cooking quality of tur when cooked as dhal and showed that a measurement of dispersed solids at a particular time of cooking of the dhals could be used for comparing the cookability of different pulses since % DS correlated very well with the cooking time of dhal being cooked. Though this provided a method for comparing the cookability of different pulses when cooked as dhals, it did not provide a method for a direct measurement of this attribute.

Reference may be made to the publication by Yusuf and Tabey (1981) where different methods for measuring cooking quality of faba beans (Vicia faba) were surveyed; They included subjective methods, use of tenderometer, penetrometer and correlate the values measured to cookability. However all these were applicable only for whole grains, based on compression or penetration of cooked grains and correlating the force required to texture in terms of 50% compression of cooked grains. These are not applicable to dhals because of small thickness and difference in the pattern of cooking between whole grains and their Pals.

Reference may be made to a method suggested by Pratape and Narasimha (1994) where the Chopin—INRA viscoelastograph was used to determine firmness of cooked dhal from soya bean. However, this method is more suitable for dhals, which do not loose shape (non-dispersible type) during cooking and hence can be applied to dhals at a stage earlier to full cooking. Moreover the instrument is rather sophisticated, expensive, and not easily affordable for all laboratories in a country like ours and needs expertise to handle. Hence it may not be very much suitable for routine use. In addition, it is based on resistance to compression and elastic recovery on release of the force applied on cooked grains and hence more suitable for whole grains rather than dhals.

Reference may be made to the publication by Matson (1946) wherein a device, named 'Bean cooker', for measuring cookability of yellow cowpeas was described. This device consisted of one hundred plunger-based unit wherein one rod was placed on each of the bean sample being cooked and the entire device was kept in a boiling water bath. Number of beans penetrated with progressive cooking was counted and the time at which 50% of the grains were penetrated was taken as cooking time. Limitations of this unit is that many dhals and whole pulses become soft even due to hydration alone and hence even though they had not attained cooked texture, they were easily penetrated. This resulted in wrong judgment of cooking time and hence does not very well meet the requirements of measuring the cooked cotyledon/dhal texture. Chinnan (1985) modified this unit for evaluating the degree of hardness in cooked beans, by introducing an electronic measuring device. However the drawbacks mentioned earlier are still associated with this modified unit also.

Rice is another cereal grain that is extremely used in the grain form after cooking to soft texture. A few attempts have been made for judging the textural softness of cooked rice and these are reviewed here. Reference may be made to the publication by Ranghino, (1966) who has suggested the pressing of cooked rice between two glass slides and observing the time at which there is disappearance of the white core and this is taken as its cooking time. However, this is very subjective (varies from person to person) and does not give a quantitative measure of the texture of cooked rice.

Reference may be made to the publication by Pillaiyar and Mohandoss (1981), who have described an impact-pressing device. Here a mild steel shaft is momentarily dropped from a pre-determined height (10 or 15 cm) on to a glass plate where the cooked rice is kept and the resulting pressed area is measured using a planimeter. Pressed area was determined for differently prepared parboiled rice sample and correlated to their sensory characteristics. They showed a relationship between the pressed areas of cooked rice to L/B ratio of the corresponding raw grains and suggested that this method could be used for differentiating differently processed parboiled rice samples. These authors, however did not suggest a method for an objective measurement of cooking time of rice being cooked. Moreover the impact system used here caused extensive mechanical damage to the cooked grains and could not be applied for judging the end point of cooking.

Sowbhagya and Ali (1990) have suggested that cooked rice attains final moisture of around 72% (wb) and could be well correlated with firmness (% F) and expansion ratio measured in a viscoelastogram. It was suggested that the grain could be considered "cooked" when it attains an F value of around 70%. This method was shown to be applicable to measure the firmness of cooked soya bean by Pratape and Narasimha, (1994). However the tests are sophisticated and may not be suitable for routine use due to non-availability of the instrument.

Need for the invention of a simple device and an objective method for judging the end point of cooking of grains like rice and dhals that could be used for routine evaluation therefore exists. Most of the methods described earlier do not give an objective and direct method for measuring the textural softness (doneness or end point of cooking) of cooked grains (dhals and rice) and current invention fulfills this gap.

OBJECTS OF THE INVENTION

It is therefore an important object of the present invention to develop a method for the direct measurement of textural softness of grains by pressing the grains at different stages of cooking and measuring the area to which it spreads, and correlating the same to the period of cooking.

Another object of the invention s to obtain a 'Spread Area' (SA) in sq. mm, against period of cooking.

Another object of the present invention is to optimize the measurement of Spread Area of rice or dhal after cooking under a standardized weight:

Another object of the present invention is to establish the relationship between the 'spread area' and 'cooking time' and provide a method for direct measurement of texture of dhals as well as rice during progressive cooking.

Yet another object of the present invention is to use the device developed for measuring the texture of different dhals and also other grains like rice in terms of SA and obtaining a relation between spread area and cooking times of different dhal samples.

Another object of the present invention is to optimize the measurement of Spread Area of rice or dhal after cooking under a standardized weight:

Another object of the present invention is to establish the relationship between the 'spread area' and 'cooking time' and provide a method for direct measurement of texture of dhals as well as rice during progressive cooking.

Yet another object of the present invention is to use the device developed for measuring the texture of different dhals and also other grains like rice in terms of SA and obtaining a relation between spread area and cooking times of different dhal samples.

SUMMARY OF THE INVENTION

These and other objects of the present invention are achieved by providing a device which enables one to obtain a plot of 'Spread Area' (SA) in sq.mm, against period of cooking. The point at which the spread area attain constancy or in some cases a sudden change in the slope of the curve is observed, is denoted as the cooking time. This is a totally new and a novel concept for determining the "doneness" of cooked grains or end point of cooking.

The present invention provides a simple device for determining the end point of cooking of grains like dhals (dehulled split pulse from different pulses) and rice wherein the 'Spread Area' of cooked grains (dhal/rice) are determined using the newly developed device in which a specified force or load is applied. The pressing device of the present invention comprises of a pressing mechanism consisting of a ram, restoring spring fulcrum link and lever; the said pressing mechanism being fixed on to a cast-iron housing, weight loading platform. The pressing mechanism is operated under a predetermined load of removable weights. Spread area is measured by projecting the image on to a screen and overlapping with an appropriate graph sheet and measuring the area in terms of sq.mm by counting. From this data the cooking time is read from the graph as the time at which there is a change of slope of the curve.

Thus, according to the present invention, there is provided a device for determining the end point of cooking of grains which comprise a ram or a plunger mounted on a housing and adapted to move linearly in said housing, a lever connected at one end to said ram and mounted on said housing, the other end of said lever being free and carrying a loading means for receiving a predetermined load of weights, a platform at the foot of said housing on which a pair of plates are placed, a sample of grains whose end point of cooking is to be determined being placed in between said plates, whereby, addition of a predetermined load of weights on the means for receiving a predetermined load weights depressing said lever downwardly causing it to push said ram downwards against said pair of plates, and thereby pressing the sample of grains contained therebetween, causing it to spread, so that the 'spread area' of said grain can be determined and measured at a regular time interval , the time at which a sudden increase or attainment of a constant value in the spread area is observed, being an indication of the cooking time of said grain.

The present invention also provides a method for determining the end point of cooking of grains which comprise placing sample grains between two plates, applying a predetermined load of weight on said pair of plates for a predetermined period of time causing said grain to spread in between said pair of plates, determining 'spread area' of said grain and measuring it at regular time intervals, the time at which a sudden increase or attainment of a constant value in the spread area is observed, being an indication of the cooking time of said grain.

In an embodiment of the invention, said lever is mounted on said housing through a fulcrum.

In an embodiment of the invention, said lever is mounted on said housing through a spring means to restore the ram to its original position after the application of force on the sample grains.

Preferably, the entire assembly of the above said component is mounted on a wooden or any other convenient base I for purposes of stability and ease of operation.

In an embodiment of the invention, the pressing can be gradual and achieved by an appropriate arrangement such as mechanical or a hydraulic mechanism in the device and wherein addition or removal of load (weights) can be manual or by alternate arrangement.

In an embodiment of the invention, arrangement is made to press more than one grain of cooked dhal or rice at a time by appropriate arrangement of uniform load on a widened disc fitted to the ram.

In an embodiment of the invention, there is provision for changing the force applied on the cooked grains by changing the weights or the dimensions of the lever or position of the fulcrum or type of lever or all of the above used for pressing in the device.

BRIEF DESCRIPTION OF THE DRAWINGS

The present invention will now be described in greater detail with reference to the accompanying drawings wherein.

The device I accordance with the present invention essentially comprises of the following components:

A lever hinged at one end and free at the other end, to transmit the load from the loading platform to the ram;

B means for receiving a predetermined load of weights (loading platform) and thus compress the sample with desired load;

C restoring spring, to facilitate quick return of the ram to original position on removal of load D ram or piston rod or plunger, to transmit the load from the lever A on to the sample E sample, grains cooked to the desired level F plates, preferably of glass to enable the grain to spread between them and to measure the area of spread G housing, material of construction being Cast Iron or any other material to house the components and offer ease of operation and stability H fulcrum link, to connect the lever A and the housing G I base, material of construction being wood or any other material to provide stability for ease of operation

DETAILED DESCRIPTION

Figure 1:
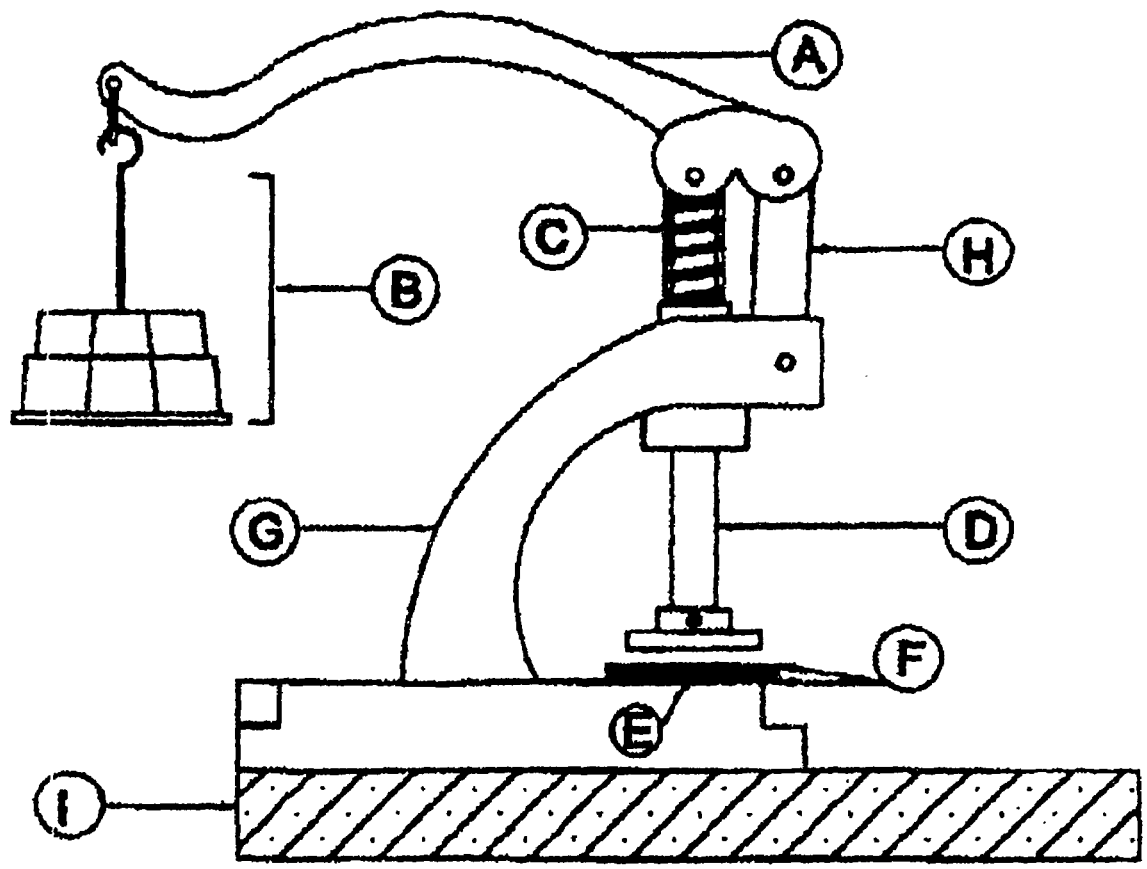
FIG. 1 is a schematic diagram of the device in accordance with the present invention.

The device as shown in FIG. 1 comprises of a ram (plunger, piston) D moving linearly in the housing G. The lever A is hinged through the fulcrum link H connected at one end to the said housing, the other free end of the said lever A carrying a loading platform B or the like to provide for placing of pre-determined load of weights on the loading platform B. Addition of known weights on the platform B depresses the lever A downwards which in turn pushes the ram D downwards against the restoring force of the spring C placed between the lever A on shed housing G concentric with the ram D. The downward movement of ram D thus, presses the cooked sample E kept between two glass plates F of suitable thickness or any other suitable plates of any other suitable material of construction. The entire assembly of the above said components is mounted on a wooden or any other convenient base I for purposes of stability and ease of operation.

In another embodiment of the present invention, the ram may be brought down gradually and gently brought in contact with the base on which the cooked dhal/rice, whose texture is to be measured, is kept. The grain is allowed to press for 30 sec. under a pre-decided constant load.

In another embodiment of the present invention, the disc fitted to the pressing end may be wide enough to press more than one grain (dhal/rice) at a time.

In another embodiment to the present invention, there is a provision for applying additional weights or removing some weights depending on the load required for pressing different grains as the need arises, could be easily carried out.

Grains (dhal or rice), cooked for different periods of time, are placed between two glass plates (F) after holding for 30 min. The assembly is kept under the ram (D). Weights (B) needed for pressing may be standardized for a particular grain (dhal or rice) prior to pressing operation. Cooked grains are kept pressed under the predetermined weights for 30 sec. and pressing operation is stopped by removing weights (B) from the hook. The 'spread area' of the cooked dhal or rice is determined and measured at a regular time interval (~5 min). However, the 'spread area' is measured every minute near the subjectively determined cooking time (SCT) of the grain being cooked. The time at which a sudden increase or attainment of a constant value in the spread area was observed, was considered as the cooking time of the dhal or rice sample (E) under examination. The load required for different grains is also standardized and indicated in the following Table, which gives the spread area of cooked grains at the respective cooking times.

Relationship between cooking time and optimized parameters in the pressing device in comparison with texture measuring system (UTM) is shown below:

| Pulse | Subjective cooking time (min) | Optimal weight needed for pressing (gm) | Spread area (at Cooking time) | UTM Hardness (N) |
| --- | --- | --- | --- | --- |
| Tur dhal | 28 | 500 | 62.1 | 3.0 |
| Green gram dhal | 18 | 300 | 25.3 | 4.0 |
| Horse gram dhal | 40 | 700 | 60.5 | 3.1 |
| Raw rice | 20 | 300 | 149.2 | 1.1 |

Figure 2:
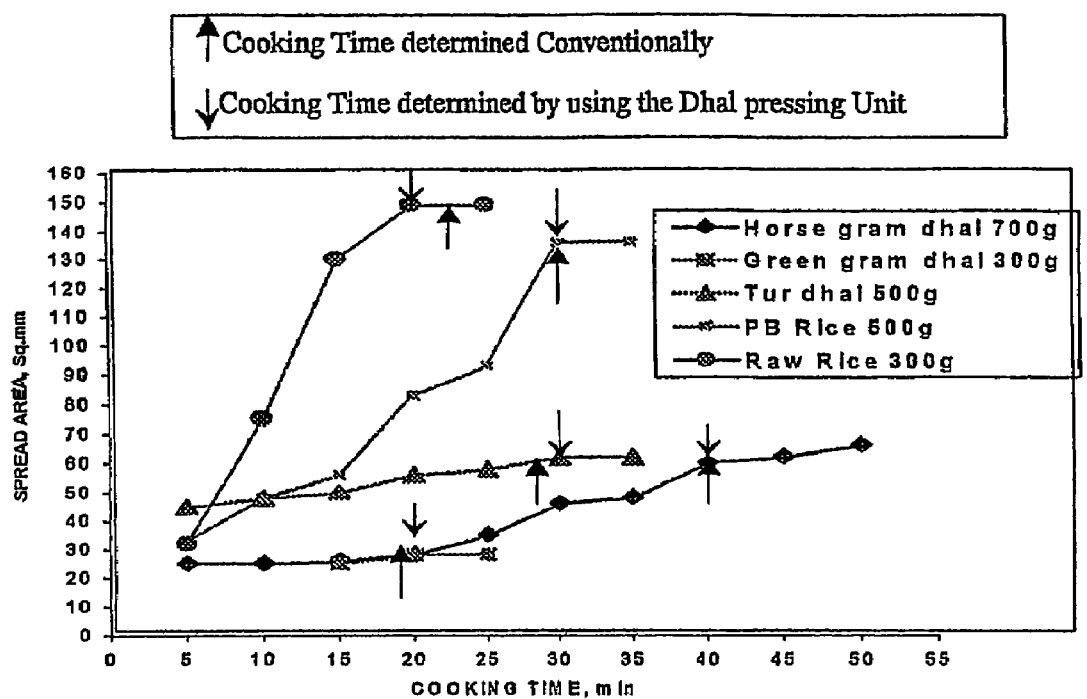
FIG. 2 is a comparative graph of the end point of cooking of grains determined by the present invention against prior art methods.

The data so collected are plotted to relate the duration of cooking and spread area as shown in FIG. 2 for different dhals as well as rice. The point at which a rapid change in slope of line occurred was shown to compound to the cooking time of the sample and therefore can be taken as "cooking time" of the dhal or rice being cooked. This was compared with other standardized method like UTM system. The value of force (N) required for 50% compression of cooked dhal sample was in good agreement with that determined using the new device.

Following examples are given by way of illustration and should not be construed to limit the scope of the present invention since it may be applicable for any such grains being cooked.

EXAMPLE 1

Dehulled and cleaned tur dhal sample was taken for cookability study. 10 g of sample was put in excess boiling water (100 ml), samples were drawn at 5 min. interval and 'spread area' measurements were carried out using the pressing device using a selected weight of 500 g as already indicated. The spread area increased gradually from about 43 sq mm (initial-soaked sample) to 59 sq mm in 25 min. and then from 59 to 63 sq. mm in the next 10 min. Therefore, the test was repeated at two-minute interval from 25 min to 35 min and a plot of spread area vs cooking time was obtained. Cooking time was noted as the time at which the spread area reached a constant value of around 62 sq. mm. The subjective cooking time of tur dhal sample being cooked was around 28 min and corresponded very well to the point at which a constant trend was observed in the graph as shown in FIG. 2 indicating that this method could be used as an objective method for evaluating the cooking time of the tur dhal being cooked.

EXAMPLE 2

10 g of cleaned dehusked green gram dhal sample were tested for cookability using the above device as indicated earlier with a selected weight of 300 g. Cooked dhal samples were removed every 5 min. intervals and the spread area was measured as indicated in example 1. The area increased gradually to about 25 sq mm in 18 min and after which there was an increase in the spread area from 25 to 28 in next 2 min. The point at which a deflection occurred is taken as the cooking time, which showed a spread area of about 27-28 sq mm at 18-19 min and corresponded to its subjective cooking time of around 18 min (FIG. 2). The spread area measurements were confirmed by repeating the experiment.

EXAMPLE 3

10 g of cleaned and dehulled horse gram dhal were tested for spread area measurements against cooking time using the above device with a selected weight of 700 g. The spread area increased gradually from 20 to 26 sq mm in 40 min and then this increased from 26 to 36 in next 10 min indicating the accomplishment of textural softness and doneness at around this time. Thus a spread area of 36 sq mm was obtained at 50 min cooking time, which corresponded to the sensory cooking time of horse gram dhal (FIG. 2 ). The test was repeated to confirm the results.

EXAMPLE 4

10 g of cleaned and polished rice was used for the measurement of spread area against period cooking using the above device with a selected weight of 300 g for raw rice. The spread area increased steadily from 10 sq mm to 134 in about 16 min. of cooking and then it is increased to 149 at 18 min. of cooking The time at which there was a sudden increase in the spread area occurred could be read from the plot as 18 minutes of cooking, which exactly coincided with the cooking time judged by conventional methods.

EXAMPLE 5

10 g of cleaned normal parboiled rice was cooked in 100 ml water and used for the measurement of spread area against period of cooking using the above device with an optimal load of 500 g. The spread area increased steadily from 19 sq mm to 94 in about 25 min. of cooking and then it increased to 112 at 27 min. of cooking which increased to about 136 sq mm in the next 3 minutes. However, it remained steady at 35 minutes of cooking. The time at which the curve showed a steady value for the Spread Area could be read from the plot as 30 minutes of cooking, which nearly coincided with the cooking time of 28 min. as judged by conventional methods. (FIG. 2).

It can be seen from the above examples that the rapid change in spread area (or a steady state in a few cases) occurred, at or near the sensory cooking time of the grain being cooked also corresponded to the time at which textural softness and doneness was achieved. Therefore this could be taken as an objective method for evaluation of the doneness of cooked grains such as dhals from different pulses as well as rice.

Novelty of the present invention is that spread area of cooked grain (rice/dhal) under a predetermined load is used for the first time as an objective method for determining the end point of cooking. Current method avoids the subjectivity of pressing cooked grains between fingers or glass slides for assessing the end point of cooking (absence of hard centres/opaque regions) as was being carried out until now.

The Main Advantages and Novelty of the Present Invention are

1. The device developed for measuring the cooking quality of grains, including dhals from different pulses, rice and such other grains, in quite simple and easy to operate.
2. Pressing the cooked grains under specified weight/force removes subjectivity in testing textural softness and enables a direct measurement of doneness or end point of cooking of the grain, in terms of spread area.
3. Pre-determined spread area for a specific dhal can be used for calibration against another standard instrumental method.
4. It can be adopted for assessing the cookability of grains (varieties of rice, dhals from different pulses and other grains) for routine laboratory evaluation.

References:
1. Subba Rao P V, Ananthachar T K, Desikachar H S R (1964) Effect of certain chemicals and pressure on cookability of pulses. Indian J Technol 2 (12): 417-418
2. Narasimha H V, Desikachar H S R (1978a) Objective methods of studying cookability of tur pulse (*Cajanus cajan*) and factors affecting varietal differences in cooking. J Food Sci Technol 15: 47-50.
3. Laignelet B, Feillet P 91979) use of viscoelastrgraph for measuring the texture of cooked rice. In: Proceedings of Chemical Aspects of Rice Grain Quality. International Rice Research Institute, Los Banos, Laguna, Phillippines, pp 355-361.
4. Ranghino, F. 1966. Valutazione delta resistenza del riso alla cottura, in base al tempo di gelatinizzazione del granelli. Riso 15: 117-127.
5. Pillayar P. and Mohandoss R (1981) A pressing device to measure the texture of cooked rice. Journal of Texture Studies, (12) 473
6. Sowbhagya C M, Ali S Z, (1991) Effect of presoaking on cooking time and texture of raw and parboiled rice J. Food Sci. Technol 28 (2) 76-80
7. Pratape V M, Narasimha H V, (1994) Processing of soybean for use as dhal. J. Food Sci. Technol, 31 (5) 423-425.
8. Youssef M M, El-Tabey A M (1981) Cooking Quality of faba beans (*Vicia faba*). Newsletter, Faba-Bean-Information-Service, No. 3, 16-17.
9. Chinnan M S, (1985) Development of a device for quantifying hard-to-cook phenomenon in cereal legumes, transactions-of-the-ASAE; 28 (1) 335-339

The invention claimed is:

1. A device for determining an end point of cooking of grains which comprises the following components: a ram or a plunger mounted on a housing and adapted to move linearly in said housing, a lever comprising first and second ends, the first end being connected to said ram and mounted on said housing, the second end of said lever being free, loading means for receiving a predetermined load of weights disposed at said second end, a platform at a foot of said housing on which a pair of plates are disposable, a sample of grains being disposable between said plates, said components being arranged such that addition of a predetermined load of weights on the loading means for receiving a predetermined load weights depresses said lever downwardly causing it to push said ram downwards against said pair of plates, and thereby presses the sample of grains contained therebetween, causing it to spread, so that an area to which the grains spread can be determined and measured at a regular time interval, the time at which a sudden increase or attainment of a constant value in the area of spread is observed being an indication of a cooking time of said grains.

2. A device as claimed in claim 1 wherein said lever is mounted on said housing through a fulcrum.

3. A device as claimed in claim 2 wherein said lever is mounted on said housing through a spring means to restore the ram to its original position after the application of force on the sample grains.

4. A device as claimed in claim 2 wherein said device is mounted on a base.

5. A kit comprising (a) the device as claimed in claim 1, and (b) means for receiving a projected image of the area of spread that facilitates measurement of the spread area at a regular time interval.

6. The kit as claimed in claim 5, wherein the means is a graph sheet.

7. The kit as claimed in claim 5, further comprising a projector for projecting an image of the spread area onto the means for receiving the projected image.

8. The kit as claimed in claim 6, further comprising a projector for projecting an image of the spread area onto the means for receiving the projected image.

9. The device as claimed in claim 1, wherein the device consists of the components.

10. A method for determining an end point of cooking of grains which comprises the steps of:
 providing the device of claim 1;
 placing sample grains between the pair of plates, applying a predetermined load of weight on said loading means so as to apply said predetermined load of weight to said pair of plates for a predetermined period of time causing said grains to spread in between said pair of plates, determining the spread area of said grains and measuring it at regular time intervals, and determining the time at which a sudden increase or attainment of a constant value in the spread area is observed to indicate the cooking time of said grains.

11. A method as claimed in claim 10 wherein said grains are cooked pulses or rice.

* * * * *